US010213210B2

(12) United States Patent
Harren et al.

(10) Patent No.: US 10,213,210 B2
(45) Date of Patent: Feb. 26, 2019

(54) VESSEL CLOSURE SYSTEM

(71) Applicant: VOSTRA-MED AG, Cham (CH)

(72) Inventors: Ersnt-Diethelm Harren, Rotkreuz (CH); Simon Ackermann, Hettlingen (CH)

(73) Assignee: VOSTRA-MED AG, Cham (CH)

( * ) Notice: Subject to any disclaimer, the term of this patent is extended or adjusted under 35 U.S.C. 154(b) by 196 days.

(21) Appl. No.: 14/653,965

(22) PCT Filed: Dec. 13, 2013

(86) PCT No.: PCT/EP2013/076570
§ 371 (c)(1),
(2) Date: Jun. 19, 2015

(87) PCT Pub. No.: WO2014/095646
PCT Pub. Date: Jun. 26, 2014

(65) Prior Publication Data
US 2015/0327869 A1    Nov. 19, 2015

(30) Foreign Application Priority Data

Dec. 21, 2012 (EP) .................................... 12405128

(51) Int. Cl.
*A61B 17/132* (2006.01)
*A61B 17/12* (2006.01)
(Continued)

(52) U.S. Cl.
CPC ............ *A61B 17/132* (2013.01); *A61B 17/12* (2013.01); *A61F 13/02* (2013.01); *A61F 13/023* (2013.01);
(Continued)

(58) Field of Classification Search
CPC .................. A61B 17/12; A61B 17/132; A61B 2017/12004
See application file for complete search history.

(56) References Cited

U.S. PATENT DOCUMENTS 268,407   A  * 12/1882  Hughes ................ A61B 17/132
                                                        24/115 H
4,592,342 A    6/1986   Salmasian
(Continued)

FOREIGN PATENT DOCUMENTS

CA       2271882 A1    5/1998
DE       4429230 A1    2/1996
(Continued)

OTHER PUBLICATIONS

Abstract of DE 4429230A1.
Abstract of DE 20 2011 106809 U1.
Abstract of EP 2404549.

*Primary Examiner* — Alexander Orkin
(74) *Attorney, Agent, or Firm* — Brian Roffe

(57) ABSTRACT

Vessel closure system that can be affixed in a spatially defined position for closing open blood vessels has a closure element, at least one pressure body arranged on the closure element and holding bands coupled to the closure element and made from a material having elastic properties. The pressure body is designed, when placed on an opened vessel of a patient, to apply increased pressure, in relation to other regions of the vessel, to a puncture site in the vessel. A skin adhesive layer is arranged on each holding band on the same side of the closure element as the pressure body. Each pressure body has a curvature projecting outwardly from the closure element such that lateral sides of the pressure body are closer to the closure element than a middle region of the pressure body between the lateral sides to provide the pressure body with an elongate pressure surface.

20 Claims, 2 Drawing Sheets

(51) Int. Cl.
*A61F 13/02* (2006.01)
*A61B 17/00* (2006.01)
*A61F 13/00* (2006.01)
*A61B 90/00* (2016.01)

(52) U.S. Cl.
CPC *A61F 13/0246* (2013.01); *A61B 2017/00902* (2013.01); *A61B 2017/00907* (2013.01); *A61B 2017/12004* (2013.01); *A61B 2090/0807* (2016.02); *A61F 2013/00468* (2013.01)

(56) References Cited

U.S. PATENT DOCUMENTS

| | | | |
|---|---|---|---|
| 4,971,046 A * | 11/1990 | Simpson | A61F 13/0203 602/43 |
| 5,269,803 A | 12/1993 | Gary et al. | |
| 5,312,350 A | 5/1994 | Jacobs | |
| 5,356,372 A * | 10/1994 | Donovan | A61F 13/023 602/41 |
| 5,376,067 A | 12/1994 | Daneshvar | |
| 5,643,315 A | 7/1997 | Daneshvar | |
| 5,690,610 A | 11/1997 | Ito et al. | |
| 6,074,356 A * | 6/2000 | Starkey | A61B 17/1325 602/75 |
| 6,274,786 B1 * | 8/2001 | Heller | A61F 13/148 128/888 |
| 6,992,232 B1 | 1/2006 | Kemeny | |
| 2005/0131329 A1 * | 6/2005 | Beaudry | A61F 5/08 602/54 |
| 2014/0277118 A1 * | 9/2014 | Harren | A61F 13/0233 606/213 |

FOREIGN PATENT DOCUMENTS

| | | |
|---|---|---|
| DE | 20 2011 106809 U1 | 11/2011 |
| EP | 0614652 A1 | 9/1994 |
| EP | 2404549 A1 | 1/2012 |
| WO | 9822027 A1 | 5/1998 |
| WO | 2006042430 A1 | 4/2006 |
| WO | 2013056383 A1 | 4/2013 |

* cited by examiner

VESSEL CLOSURE SYSTEM

FIELD OF THE INVENTION

The invention relates to a vessel closure system including holding bands and a closure element with at least one pressure body that has a pressure surface.

In particular, the invention relates to a vessel closure system for securing the puncture point in the skin and the puncture site of opened vessels before secondary bleeding and which is used for the permanent visual checking for any escaping blood. Likewise, with said system it should be possible to achieve tactile and acoustic control of unchecked blood flow within the vessel.

The invention relates in particular to a vessel closure system that can be affixed in a spatially defined position for securing open vessels before secondary bleeding, comprising at least one pressure body which is suitable for coming into contact with a wound.

BACKGROUND OF THE INVENTION

Vessel closure systems are effective in relation to the time required for bleeding to stop. In this field of medical applications, in particular however in the opening of vessels for interventional invasions, there is still a requirement to make available a closure for opened vessels that is also easy for qualified medical staff to handle with which not only is blood escaping subsequently or blood loss into the free space outside of the body prevented, but also the passing of blood into the tissue (haematoma formation) is prevented, at the same time however the vital circulation of blood within the body after insertion and final positioning of the vessel closure being proven to be unimpeded.

Generally, the closure of opened vessels takes place such that, following intervention at the puncture point and the vessel puncture site, manual pressure is at the same time exerted to the correct extent. Due to the risk of haematoma formation the pressure must not be too low, and due to the risk of circulation prevention in the respective body part, it must however not be too great either.

After bleeding has stopped, mechanical aids are fastened to the body with bandages so that the mechanical aid continues to provide compression in conjunction with the bandage.

OBJECTS AND SUMMARY OF THE INVENTION

It is the object of the present invention to disclose a vessel closure system that is free from complication.

The vessel closure system according to the invention makes it possible, in a surprisingly easy manner, to apply a pressure that can be set in each individual case by tensile force, to the vessel opening. Furthermore, a vessel closure system is easily provided with which a different closure element geometry is made available. In contrast to closure systems from the prior art one can therefore take into account that the puncture point on the skin and the vessel puncture site are on different levels. Perfect closure of these puncture sites is thus provided.

If necessary, by pressing on the rear side of the pressure body, temporary, supporting compression can be provided. Upon leaving the medical facility, the patients can leave the vessel closure system at the puncture site.

Preferably, the at least one pressure body is designed such that by means of the latter, pressure which is reduced in relation to the puncture site within the vessel is applied to a region in order to measure the pulse on the vessel. In this way the vessel closure system can be supplemented by a pulse measuring sensor that optionally detects blood congestion before this occurs. The transparent pressure body allows unlimited observation of the puncture point. Likewise, by attaching a blood pressure measuring device it is possible to monitor unchecked blood flow within the vessel permanently by means of a sensor.

Preferably, the at least one pressure body replicates the anatomical form of a finger in order to manually close the puncture point in the skin or of the punctured vessel. This type of vessel closure system can be used in different ways. The vessel closure system can either be used as the primary closure, i.e. the vessel closure system is applied immediately after the invasive intervention, or is used as a secondary closure system with which the doctor carrying out the procedure manually presses the puncture point in the skin and the vessel puncture site at the same time after the invasive intervention until the blood flow has been stopped. After this the doctor carrying out the procedure positions the vessel closure system so that both the puncture point in the skin and the vessel puncture site are covered.

Within the framework of the invention the anatomical form of the pressure body corresponds to a replication of three fingers, preferably with the middle finger.

In one particular embodiment the pressure body is disposed in the longitudinal extension of the holding bands.

Furthermore, the vessel closure system can have a plurality of holding bands which are connected to distal ends of the closure element, the holding bands having non-elastic properties.

BRIEF DESCRIPTION OF THE DRAWINGS

Preferably, the closure element and the holding bands are made in one piece. Here the vessel closure system is provided with appropriately long holding bands. As well as good manageability, sufficient adhesion to the skin should thus also be achieved in order to be able to establish the counter pressure required to stop bleeding.

Preferably, a reinforcement layer, which is made of a material with non-elastic properties, is respectively attached to a side of the vessel closure system on which the at least one pressure body is provided in the region of the holding bands. By means of this reinforcement layer the holding bands are provided with the necessary non-elastic properties.

DETAILED DESCRIPTION OF THE INVENTION

Advantageously, the reinforcement layer is connected on one side respectively to the region of the holding bands by means of an adhesive and is provided on the other side with a skin adhesive layer. With the aid of the skin adhesive layer the vessel closure system is fixed onto the patient's skin such that in this way the pressure body reliably closes the puncture opening.

The skin adhesive layer can be covered with a removable protective film. In this way the skin adhesive layer is protected, and so guarantees a long-lasting adhesive force of the skin adhesive layer.

Preferably, the closure element and/or the at least one pressure body and/or the holding bands and/or the reinforcement layer are transparent or almost transparent. In this way the application of the vessel closure system as a puncture closure at the correct position is facilitated. A transparent pressure body allows one to observe the puncture point without any restriction.

Preferably, the vessel closure system also includes a receiver for a pulse frequency sensor.

Figure 1:
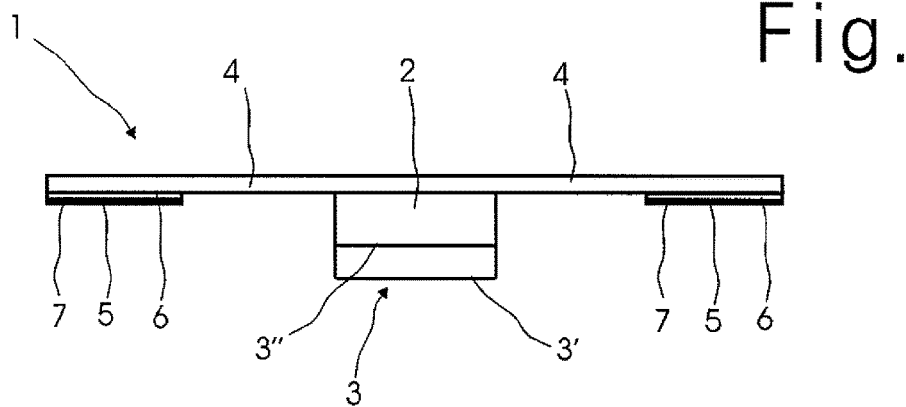
Figure 2:
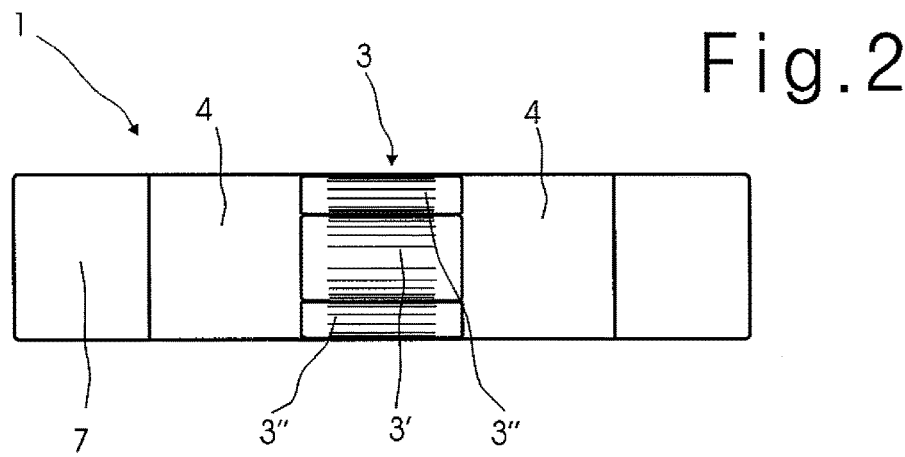
Figure 3:
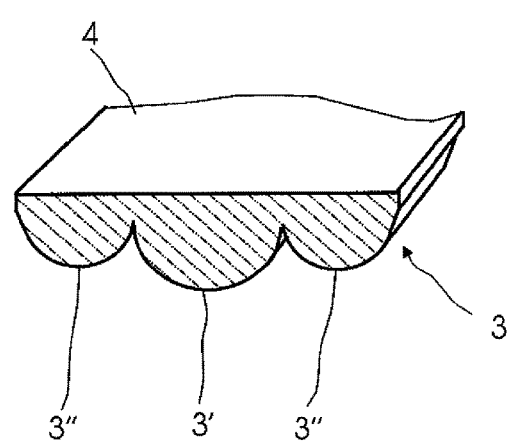
Figure 4:
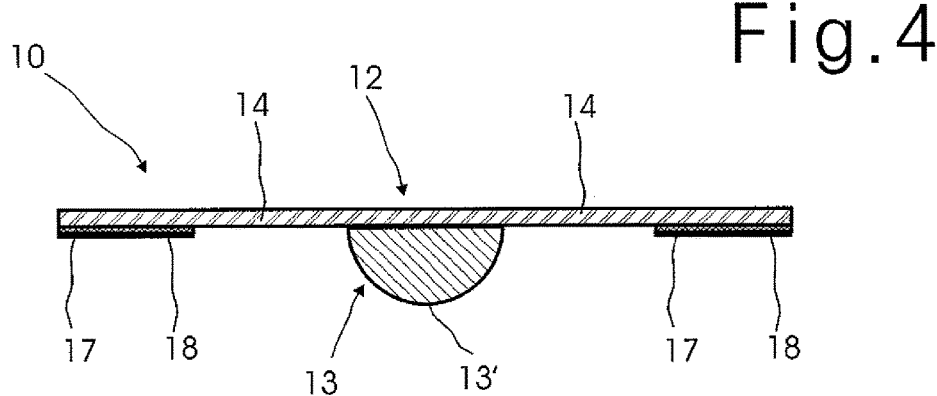
Figure 5:
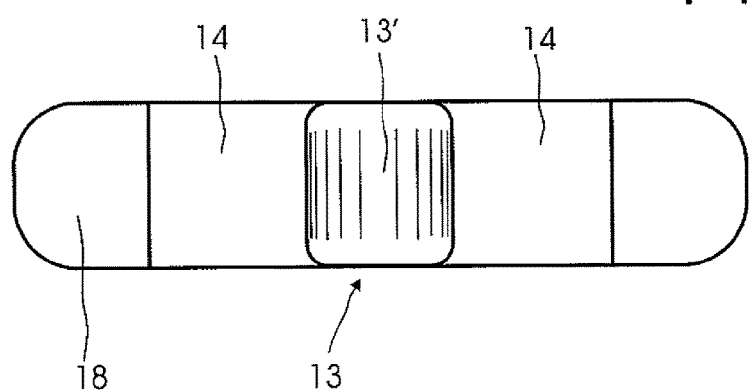

Exemplary embodiments of the invention are described in more detail by means of the drawings. These show as follows:

FIG. 1 is a view of a vessel closure system according to the invention that can be affixed;

FIG. 2 is a view from below of the vessel closure system according to FIG. 1;

FIG. 3 is a cross-section of the partially shown vessel closure system;

FIG. 4 is a longitudinal section through a version of a vessel closure system; and FIG. 5 is a view from below of the vessel closure system according to FIG. 4.

FIG. 1 and FIG. 4 show a vessel closure system 1 that can be affixed and which includes a closure element 2 and at least one pressure body 3 which, in this example, are made in one piece from a material having elastic properties, for example silicon.

According to the invention, the pressure body 3 is shaped such that when placed on an opened vessel of a patient, it generates increased pressure. In other words, the pressure body 3 applies reduced pressure in relation to the puncture site in the vessel to a puncture point on the skin and reduced pressure in relation to the puncture site within the vessel to a region for measuring pulse on the vessel.

The pressure body 3 is made in the anatomical form of three fingers. In this connection the middle finger replica of the total of three finger replicas protrudes in relation to the fingers lying on either side. Overall, the anatomical form of the finger replicas is adapted to a puncture site within the vessel, to a puncture point on the skin or to a region for pulse measurement on the vessel.

Advantageously, the three pressure bodies 3 formed are each arranged with an elongate pressure surface 3', 3" in the direction of the holding bands 4. The two outer pressure surfaces 3" are somewhat set back height-wise here in comparison to the middle pressure surface 3'. Optimal pressing of the closure at the puncture site of the vessel is thus produced.

Furthermore, two holding bands 4 forming the two ends of the closure element 2 are provided. The holding bands 4 have non-elastic properties. For example, the holding bands 4 and the closure element 2 can be made in one piece. In order to provide the holding bands 4 with the non-elastic properties, a reinforcement layer 5 is applied to the holding bands 4. The reinforcement layer 5 can be affixed to the holding bands 4 by means of a conventional adhesive 6. In order to improve the long-term contact of silicon with the adhesive used 6, a surface treatment such as e.g. a plasma, corona, wet-chemical or other treatment can therefore be provided.

Alternatively, the common material from which the closure element 2, the pressure body 3 and the holding bands 4 are made in one piece can be processed by means of specific curing processing procedures such that only the material in the region of the holding bands 4 does not allow expansion, while the other regions are still expandable.

In principle, the holding bands 4 and the closure element 2 can be made of different materials which are connected to one another. Here the closure element 2 can be made of silicon and the holding bands 4 can be made of polyethylene (PE).

On the lower side of the reinforcement layer 5 a skin adhesive layer 7 is provided for adhesion to the skin. The skin adhesive layer 7 preferably has skin adhesive-specific properties. Finally, the skin adhesive layer 7 can additionally also be provided with a removable protective film (not shown).

The closure element 2, the at least one anatomically replicated pressure body 3, the holding bands 4 and the reinforcement layer 5 are preferably made to be transparent or almost transparent in order to facilitate the application of the vessel closure system 1 that can be affixed in a spatially defined position.

As well as exceptional expansibility, silicon also has a desirably high restoring force. However, other materials such as e.g. natural rubber, synthetic rubber, gum, latex, hydrogel, polymer plastic or a combination of these materials can also be used. Alternatively, the holding bands can be produced from polyethylene (PE).

In normal cases (for example after examination and/or treatment etc.) the anatomically replicated pressure body 3 is directly in contact with the skin. Therefore, suitable medical properties are required for the materials used, especially with regard to skin and body compatibility.

Before a needle or cannula is removed from the puncture site, the corresponding point on the body is cleaned and disinfected in a conventional manner. Then, the protective films are removed from both holding bands of the vessel closure system 1. The vessel closure system 1 is then placed on and fixed to the respective point on the body by means of the holding bands 4 such that when the vessel closure system 1 is subsequently fully applied, the pressure body 3 is positioned such that maximum pressure is applied to the puncture site of the vessel. In addition, the pressure body 3 is positioned such that increased pressure is applied to the puncture point on the patient's skin.

Furthermore, increased pressure is applied to a region for measuring pulse on the vessel. It should be noted here that the two latterly specified pressures are less than the pressure which is applied to the puncture site of the vessel. In this way, similarly to the manual application of pressure to an opened vessel by a medical professional, maximum pressure is applied to the puncture site of the vessel while, in relation to this, less pressure is applied to the puncture point on the skin so as to thus guarantee an unobstructed blood supply. Then, the needle, cannula, port or catheter is removed.

Specified as fields of application for the vessel closure system 1 are: vessel closure system for closing vessels after interventional invasions with catheters via the radial, femoral, cubital or brachial artery; in general medicine before removing in-dwelling catheters; in vascular surgery after removing varicose veins; after minimally invasive surgical interventions before removing medical instruments.

In the aforementioned application of the vessel closure system according to the invention as a closure system for closing vessels, the vessel closure system is applied e.g. following a coronary intervention. Coronary interventions are almost exclusively carried out via the radial or the femoral artery. Arterial closure systems are developed with the aim of reducing the time to haemostasis and at the same time of preventing or reducing peripheral vascular complications. A further reduced haemostasis time in comparison to the prior art, with at the same time prevention of peripheral vascular complications, is achieved by the vessel closure system according to the invention.

By stretching the vessel closure system 1 by applying a tensile force to each of the holding bands 4, the length of the closure element 2 alone is stretched due to the elastic property of the material of the latter.

FIG. 4 and FIG. 5 show a version of a vessel closure system 10 with an elastic closure element 12 and a pressure body 13. The latter has a pressure surface 13' which, when applied, comes substantially into contact with the skin.

According to the invention, the pressure body 13 has an elongate, straight pressure surface 13' that runs transversely to the longitudinal extension of the holding bands 14. Very advantageously, this pressure surface 13' is disposed over almost the entire width and at right angles to the holding bands 14. This pressure body 13 is made in the replica form of a phalanx and is affixed as a separate part to the holding bands 14, for example. This results in inexpensive production of the closure.

Thus, when placed on an opened vessel of a patient, increased pressure can be achieved at a puncture site within the vessel in relation to other regions of the vessel.

Furthermore, there is at least one skin adhesive layer 17 for affixing to the skin and a removable protective film 18 on the lower side of the holding bands 14.

The invention claimed is:

1. A vessel closure system that closes an open vessel in a body, comprising:
    elastic holding bands, each of the holding bands having a lower side and an exposed upper side;
    a closure element coupled to and arranged between the holding bands, the closure element having a lower side and an exposed upper side, the upper side of the holding bands and the upper side of the closure element being an upper side of the closure system;
    first, second and third pressure bodies arranged entirely on the lower side of the closure element and each defining an elongate pressure surface, each of the first, second and third pressure bodies having a curvature projecting outwardly from the closure element such that lateral sides of the first, second and third pressure bodies are closer to the closure element than a middle region of the first, second and third pressure bodies between the lateral sides, each of the first, second and third pressure bodies having a rectangular shape with first and second opposed edge regions, the first and second edge regions being adjacent a respective one of the holding bands; and
    a skin adhesive layer arranged on the lower side of each of the holding bands such that the skin adhesive layer and the first, second and third pressure bodies are on a common side of the closure system,
    the first, second and third pressure bodies in combination having an anatomical shape of three elongate fingers which are alongside one another the first, second and third pressure bodies each constituting one of the three elongate fingers, the first pressure body being adjacent a first lateral side of the closure element, the second pressure body being adjacent a second lateral side of the closure element opposite the first lateral side of the closure element, and the third pressure body being situated between the first and second pressure bodies and having a larger height in a middle region than a height of the first and second pressure bodies in a middle region,
    the first, second and third pressure bodies having an outer surface that constitutes an outer patient-contacting surface of the vessel closure system and has skin and body compatibility properties that enable the first, second and third pressure bodies to directly contact skin and body of the patient,
    whereby when the vessel closure system is placed on an open, punctured vessel, the skin adhesive layer is adhered to the skin of the patient with the first, second and third pressure bodies situated at a puncture site within the vessel and the outer surface of the first, second and third pressure bodies in contact with the skin of the patient.

2. The vessel closure system according to claim 1, wherein the first, second and third pressure bodies extend in a direction between the holding bands.

3. The vessel closure system according to claim 1, wherein the first, second and third pressure bodies in combination extend over an entire width of the holding bands.

4. The vessel closure system according to claim 1, wherein the closure element has first and second opposed edge regions, one of the holding bands being coupled to the first edge region of the closure element and another one of the holding bands being coupled to the second edge region of the closure element, the first, second and third pressure bodies each extending linearly in a longitudinal direction from the one of the holding bands to the another one of the holding bands such that the lateral sides of each of the first, second and third pressure bodies run in the longitudinal direction.

5. The vessel closure system according to claim 1, wherein the closure element and the holding bands are made in one piece.

6. The vessel closure system according to claim 1, wherein the closure element and the holding bands are made in a number of pieces.

7. The vessel closure system according to claim 1, further comprising a reinforcement layer arranged at an end region of each holding band, each reinforcement layer comprising a material with non-elastic properties such that each of the holding bands has a non-elastic portion in the respective end region and an elastic portion between the non-elastic portion and the closure element.

8. The vessel closure system according to claim 7, wherein each reinforcement layer has a first side and a second side and is connected on the first side to the respective holding band by adhesive and is connected on the second side to the skin adhesive layer.

9. The vessel closure system according to claim 7, wherein at least one of the closure element, the first, second and third pressure bodies, the holding bands, and the reinforcement layers is transparent.

10. The vessel closure system according to claim 1, wherein the skin adhesive layer is configured to be covered by a removable protective film.

11. The vessel closure system according to claim 1, wherein at least one of the closure element, the first, second and third pressure bodies and the holding bands are made of silicon, natural rubber, synthetic rubber, gum, latex, hydrogel, polymer plastic or a combination of these materials.

12. The vessel closure system according to claim 1, wherein at least one of the closure element, the first, second and third pressure bodies and the holding bands, are transparent.

13. The vessel closure system according to claim 1, wherein the closure element and the first, second and third pressure bodies are transparent.

14. The vessel closure system according to claim 1, wherein the closure element and the holding band are dimensioned to provide the vessel closure system with a generally rectangular shape.

15. The vessel closure system according to claim 1, wherein the closure element and the first, second and third pressure bodies are made in one piece from a material having elastic properties.

16. The vessel closure system according to claim 1, wherein the first, second and third pressure bodies are separated by straight linear lines.

17. The vessel closure system according to claim 1, wherein the closure element and the first, second and third pressure bodies are made from material having elastic properties and each of the holding bands has a non-elastic portion in a respective end region and an elastic portion between the non-elastic portion and the closure element such that the closure device is entirely elastic between the non-elastic portions of the holding bands.

18. The vessel closure system according to claim 1, wherein the vessel closure system has a rectangular shape and the first, second and third pressure bodies in combination extend over an entire width of the holding bands.

19. The vessel closure system according to claim 1, wherein the closure element and the first, second and third pressure bodies consist of material having elastic properties such that the vessel closure system is entirely elastic between the holding bands.

20. The vessel closure system according to claim 1, wherein the elongate pressure surface of each of the first, second and third pressure bodies is a straight linear formed top surface.

\* \* \* \* \*